United States Patent
McDonnell et al.

(10) Patent No.: US 7,217,685 B2
(45) Date of Patent: May 15, 2007

(54) CLEANING AND DECONTAMINATION FORMULA FOR SURFACES CONTAMINATED WITH PRION-INFECTED MATERIAL

(75) Inventors: Gerald E. McDonnell, Basingstoke (GB); Herbert J. Kaiser, Pontoon Beach, IL (US); Kathleen M. Antloga, Chardon, OH (US); Mildred R. Bernardo, St. Louis, MO (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 11/430,699

(22) Filed: May 9, 2006

(65) Prior Publication Data

US 2007/0037723 A1    Feb. 15, 2007

Related U.S. Application Data

(62) Division of application No. 10/448,910, filed on May 30, 2003, now Pat. No. 7,071,152.

(51) Int. Cl.
*C11D 3/395* (2006.01)
*C11D 3/43* (2006.01)

(52) U.S. Cl. .............. 510/161; 510/367; 510/372; 510/432; 510/199; 510/202; 510/245; 510/255; 510/258; 510/271

(58) Field of Classification Search .......... 510/161, 510/367, 372, 432, 199, 202, 245, 255, 258, 510/271
See application file for complete search history.

(56) References Cited

U.S. PATENT DOCUMENTS

| | | |
|---|---|---|
| 3,941,696 A | 3/1976 | Melnick et al. |
| 4,169,123 A | 9/1979 | Moore et al. |
| 4,973,449 A | 11/1990 | Kolstad et al. |
| 5,007,232 A | 4/1991 | Caudill |
| 5,116,575 A | 5/1992 | Badertscher et al. |
| 5,145,642 A | 9/1992 | Feathers, III et al. |
| 5,173,259 A | 12/1992 | Bordini |
| 5,178,841 A | 1/1993 | Vokins et al. |
| 5,258,162 A | 11/1993 | Andersson et al. |
| 5,513,662 A * | 5/1996 | Morse et al. ............ 128/898 |
| 5,567,444 A | 10/1996 | Hei et al. |
| 5,600,142 A | 2/1997 | Van den Berg et al. |
| 5,634,880 A | 6/1997 | Feldman et al. |
| 5,674,450 A | 10/1997 | Lin et al. |
| 5,733,503 A | 3/1998 | Kowatsch et al. |
| 5,756,678 A | 5/1998 | Shenoy et al. |
| 5,779,973 A | 7/1998 | Edwards et al. |
| 5,788,925 A | 8/1998 | Pai et al. |
| 5,792,435 A | 8/1998 | Mueller et al. |
| 5,837,193 A | 11/1998 | Childers et al. |
| 5,848,515 A | 12/1998 | Catelli et al. |
| 5,872,359 A | 2/1999 | Stewart et al. |
| 5,876,664 A | 3/1999 | Childers et al. |
| 6,094,523 A | 7/2000 | Zelina et al. |
| 6,448,062 B1 | 9/2002 | Huth et al. |
| 6,696,074 B2 | 2/2004 | Dai et al. |
| 6,734,405 B2 * | 5/2004 | Centanni et al. ......... 219/628 |
| 2002/0168289 A1 * | 11/2002 | McVey .................... 422/28 |
| 2003/0086820 A1 | 5/2003 | McDonnell et al. |
| 2006/0008494 A1 * | 1/2006 | Prusiner ................. 424/405 |
| 2006/0104858 A1 * | 5/2006 | Potember et al. .......... 422/4 |

FOREIGN PATENT DOCUMENTS

| | | |
|---|---|---|
| EP | 774 263 A1 | 5/1997 |
| FR | 2759589 | 8/1998 |
| GB | 2391785 A | 2/2004 |
| WO | WO 94/22305 | 10/1994 |
| WO | WO 98/15297 | 4/1998 |
| WO | WO 01/54736 A2 | 8/2001 |

OTHER PUBLICATIONS

GMT Global Medical Technologies, Ltd. Product Information "Ecocycle 10" http://www.globalmedicaltechnologies.com/view_prd.php?code=bw0002 Sep. 15, 2005.
MSDS data sheet for the STERIS 20® Sterilant Concentrate.
Rutala, et al., "Creutzfeldt-Jakob Disease: Recommendations for Disinfection and Sterilization", Clinical Infectious Diseases, V. 32, N. 9, May 2001, pp. 1348-1356 XP008012867.
Darbord, "Inactivation of Prions in Daily Medical Practice", Biomedicine & Pharmacotherapy, V. 53, 1999, pp. 34-38 XP002228686.
Samson, "Stérilisation du material de dermato-chirurgie au cabinet du dermatologue" Nouvelle Dermatologiques, V. 19, N. 1, 2000 pp. 57-60 XP008012868.
Disinfection, Sterilization and Preservation (Ed. S.S. Block); 4th Ed. pp. 436-439.

* cited by examiner

*Primary Examiner*—Charles Boyer
(74) *Attorney, Agent, or Firm*—Fay Sharpe LLP

(57) ABSTRACT

A method of treating the surfaces of medical instruments which are contaminated with prions includes contacting the surface with a composition containing a source of peroxide ions, such as hydrogen peroxide, at a molar concentration of at least 1.5M peroxide (equivalent to approximately 5% hydrogen peroxide) and preferably, about 2M peroxide (approximately 7% hydrogen peroxide). The composition is optionally in the form of a gel. The composition is retained in contact with the surfaces for about 1–2 hours until all or substantially all prion contamination is removed.

10 Claims, 1 Drawing Sheet

US 7,217,685 B2

CLEANING AND DECONTAMINATION FORMULA FOR SURFACES CONTAMINATED WITH PRION-INFECTED MATERIAL

This application claims the benefit, as a divisional application, of application Ser. No. 10/448,910, filed May 30, 2003 now U.S. Pat. No. 7,071,152, which is incorporated herein by reference in its entirety.

BACKGROUND OF THE INVENTION

The present invention relates to the field of biological decontamination. The invention finds particular application in connection with the cleaning and removal and/or destruction of harmful biological materials, such as prions (proteinaceous-infectious agents), from medical, dental, and pharmaceutical instruments and will be described with particular reference thereto. It will be appreciated, however, that the method and system of the present invention may be utilized in biological decontamination of a wide range of equipment, instruments, and other surfaces contaminated with prion infected material, such as pharmaceutical preparation facilities, food processing facilities, laboratory animal research facilities including floors, work surfaces, equipment, cages, fermentation tanks, fluid lines, and the like.

The term "Prion" is used to describe proteinaceous-infectious agents that cause relatively similar brain diseases in humans and/or in animals, which are invariably fatal. These diseases are generally referred to as transmissible spongiform encephalopathies (TSEs). TSEs include Creutzfeldt-Jakob disease (CJD) and variant CJD (vCJD) in humans, Bovine Spongiform Encephalopathy (BSE) in cattle, also know as "Mad Cow Disease," Scrapie in sheep, and Wasting Disease in elk. All of these diseases attack the neurological organs of the animal or animals which are susceptible to the particular disease. They are characterized by initially long incubation times followed by a short period of neurological symptoms, including dementia and loss of coordination, and eventually death.

The infectious agent responsible for these diseases is thought to be a simple protein, with no associated nucleic acids. The pathogenic mechanism for such prion diseases is proposed to involve an initially normal host encoded protein. The protein undergoes a conformational change to an abnormal form (a prion), which has the ability of self-propagation. The exact cause of this change is, at present, unknown. The abnormal form of the protein is not broken down effectively in the body and its accumulation in certain tissues (in particular neural tissue) eventually causes tissue damage, such as cell death. Once significant neural tissue damage has occurred, the clinical signs are observed.

Prion diseases may thus be classified as protein aggregation diseases, which also include several other fatal diseases, such as Alzheimer's disease and amyloidosis. In the case of CJD, the most prevalent prion disease in humans (occurring in roughly 1:1,000,000 of the population), about 85% of cases are thought to arise sporadically, about 10% are thought to be inherited, and about 5% arise iatrogenically.

Although not considered to be highly contagious, prion diseases can be transmitted by certain high risk tissues, including the brain, spinal cord, cerebral spinal fluids, and the eye. After a surgical procedure on a prion infected patient, prion containing residue may remain on the surgical instruments, particularly neurosurgical and ophthalmological instruments. During the long incubation period, it is extremely difficult to determine whether a surgical candidate is a prion carrier.

Different levels of microbial decontamination are recognized in the art. For example, sanitizing connotes free from dirt or germs by cleaning. Disinfecting calls for cleansing in order to destroy harmful microorganisms. Sterilization, the highest level of biological contamination control, connotes the destruction of all living microorganisms.

It is now known that certain biological materials, which do not live or reproduce in the conventional sense, such as prions, are nevertheless capable of replication and/or transformation into harmful entities. We use herein the term "deactivation" to encompass the destruction of such harmful biological materials, such as prions, and/or their ability to replicate or undergo conformational changes to harmful species.

Liquid sterilization systems, such as those employing peracetic acid and hydrogen peroxide are widely used for microbial decontamination. Prions, however, are notoriously very hardy and demonstrate resistance to routine methods of decontamination and sterilization. Unlike microorganisms, prions have no DNA or RNA to destroy or disrupt. Prions, due to their hydrophobic nature, tend to aggregate together in insoluble clumps. Under many conditions that lead to successful sterilization in microorganisms, prions form tighter clumps, which protect themselves and underlying prions from the sterilization process. The World Health Organization (1997) protocol for prion deactivation calls for soaking the instrument in concentrated sodium hydroxide or hypochlorite for two hours followed by one hour in an autoclave. Other suggested methods include prolonged steam sterilization. These aggressive treatments are often incompatible with medical devices, particularly flexible endoscopes and other devices with plastic, brass, or aluminum parts. Many devices are damaged by exposure to high temperatures. Chemical treatments, such as strong alkali, are damaging to medical device materials or surfaces in general. Glutaraldehyde, formaldehyde, ethylene oxide, liquid hydrogen peroxide, most phenolics, alcohols, and processes such as dry heat, boiling, freezing, UV, ionizing, and microwave radiation have generally been reported to be ineffective. For example, a solution of 3% hydrogen peroxide in water was found to be ineffective against prions (Brown, et al., *J. Infectious Diseases*, vol. 145, No. 5, pp. 683–687 (May 1982). There is a clear need for products and processes that are effective against prions yet compatible with surfaces.

The present invention provides a new and improved composition and method of treatment of surfaces contaminated with prion-infected material which overcome the above-referenced problems and others.

SUMMARY OF THE INVENTION

In accordance with one aspect of the present invention, a method of treatment of a prion-contaminated surface is provided. The method includes contacting the surface with an aqueous composition containing at least 5% by weight of hydrogen peroxide for sufficient time to at least substantially reduce prions on the surface.

In accordance with another aspect of the present invention, a method for treatment of a device contaminated with prions is provided. The method includes coating surfaces of the device with a gel composition which includes peroxide at a molar concentration of at least 1.5 M and a humectant. The gel is retained in contact with the surfaces for at least one hour.

In accordance with another aspect of the present invention, a composition for treatment of prion contaminated surfaces is provided. The composition includes 5–30% by weight hydrogen peroxide, a thickener in a sufficient amount to provide a viscosity of 700–4000 cps, 5–30% by weight of a humectant, at least 0.1% by weight of a corrosion inhibitor, and a hydrogen peroxide stabilizer.

One advantage of at least one embodiment of the present invention is that it is gentle on instruments.

Another advantage of at least one embodiment of the present invention is that it deactivates prions quickly and effectively.

Another advantage of at least one embodiment of the present invention is that it is compatible with a wide variety of materials and devices.

Another advantage of at least one embodiment of the present invention is that it enables cleaning and decontamination to be carried out in a single step.

Another advantage of at least one embodiment of the present invention is that cross-contamination of medical instruments and cleaning equipment and hazards to healthcare workers during a cleaning process are reduced.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
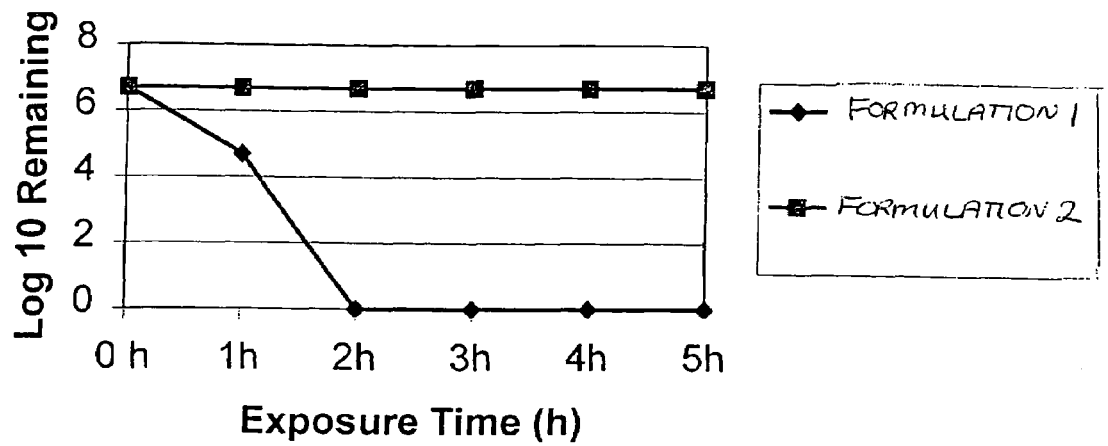
FIG. 1 is a plot of the number of ileal fluid dependent organism(s) (IFDO) remaining over time when exposed to a composition according to the present invention and to a control formulation.
Figure 2:
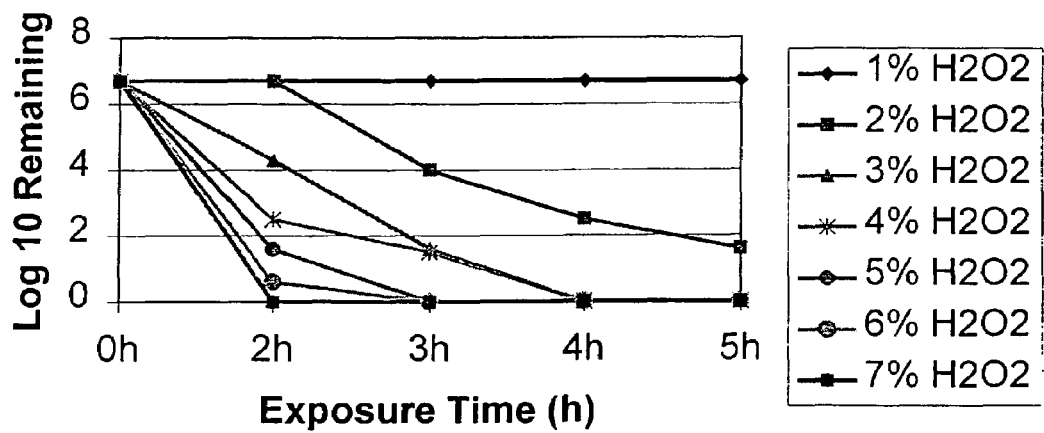
FIG. 2 is a plot of the number of IFDO remaining over time when exposed to compositions containing from 1% to 7% by weight hydrogen peroxide.

A method of decontaminating surfaces contaminated with prions includes contacting the surface to be treated with a composition which includes hydrogen peroxide at a sufficient concentration and for a sufficient time to remove prions from the surface and/or destroy prions on the surface. It has unexpectedly been found that by treating prions with hydrogen peroxide in an aqueous composition at relatively high concentrations (i.e., above about 5% by weight of the composition is hydrogen peroxide or an equivalent molar percent of peroxide), substantial (i.e., greater than 99% destruction) of prions is achieved in a relatively short time (about one hour, or less). A six log reduction (no more than 1 of every million prions initially present remains) is achieved in under three hours, more preferably, in about two hours or less.

The treatment is effective against human prions (i.e., prions capable of replication within humans), as well as prions found in other animal species, such as cattle, sheep, and mice. For example, prions responsible from CJD and vCJD in humans, BSE in cattle, and scrapie in sheep are removed. The prions are typically present in biological fluids and animal tissue, such as blood, brain or nervous system tissue. Accordingly, it is preferable to treat the contaminated surface with a cleaning composition formulated to remove the biological fluids or tissue such that prions remaining on the surface are readily accessed by the hydrogen peroxide and deactivated.

A composition is provided for treatment of items, such as medical equipment, pharmaceutical equipment, mortuary equipment, meat processing equipment, food handling equipment, and the like. It is particularly suited to the treatment of medical instruments and other medical devices which have been employed in a surgical operation, such as scalpels, scissors, endoscopes, forceps, catheters, retractors, clamps, spatulas, and the like, and will be described with particular reference thereto.

The composition is preferably in the form of a liquid or a thickened composition, such as a gel or foam, which is applied to the items to be treated. Suitable application methods include spraying the composition over the items to be decontaminated, applying the composition with an applicator, such as a brush or roller, or dipping or immersing the items in the composition. The contacting may be accompanied by agitation or scrubbing to increase penetration of the composition and aid in removal of biological matter.

For medical instruments, a preferred composition is in the form of a gel or similar thickened composition. The gel retains the composition on the instruments for an extended period so that instruments which are contaminated with prion infected body fluids or tissue do not dry out before cleaning is complete. If contaminated instruments are allowed to dry completely, the body fluids harden and become hard to remove. The dried residues are more difficult for hydrogen peroxide to penetrate and destroy remaining prions. The thickened composition containing hydrogen peroxide prevents the instruments from drying out for extended periods, such as for two or more hours, more preferably, at least four hours, and up to eight or more hours—i.e., long enough for the items to be transported to a reprocessing area and receive further treatment.

The gel or liquid composition allows the instruments to be transferred safely from a surgery or other site at which the instruments are used to a reprocessing area where further decontamination processes take place, such as further cleaning, sterilization, disinfection, or the like.

For treatment of larger areas, such as walls, work surfaces, and large equipment, a liquid composition is suitable.

In addition to destroying prions on the contaminated devices, the composition is also effective to provide low level disinfection of harmful viruses, such as HIB, HIV, HBV, and MRSA. Other proteins on the devices are also broken down or deactivated, rendering them easier to remove from the devices.

The composition is preferably aqueous, although use of other solvents, such as organic solvents in the composition is also contemplated. In addition to water, the composition includes a source of peroxide. The source of peroxide preferably includes hydrogen peroxide at a concentration of at least 5% by weight and can be up to about 30% by weight, more preferably, about 6–8% by weight, and most preferably, about 7% by weight hydrogen peroxide. While higher concentrations of hydrogen peroxide are contemplated, a composition containing about 7% has been found effective at removing all traces of prions (at least a six log reduction) in about two hours, or less. About 99% of the prions are destroyed in about 1 hour.

Hydrogen peroxide is commercially available as an approximately 3–55% solution in water, typically at about 35%, which is then diluted by water and other components of the composition to the desired level.

Other sources of peroxide which yield peroxide ions in an equivalent molar amount are also contemplated. For example, the composition may include reagents which form peroxide ions on mixing. Preferably, the peroxide in the composition is at a molar concentration of at least 1.75 M (moles/liter), equivalent to a hydrogen peroxide concentration of 5% by weight, more preferably, at least about 2.18 M, equivalent to a hydrogen peroxide concentration of 6% by weight, and most preferably, about 2.64 M (equivalent to a 7% hydrogen peroxide solution).

The composition optionally includes a thickener to provide the composition with a viscosity of about 500 centipoise (cps), or higher. The composition has a sufficient viscosity such that it coats the instruments and inhibits drying of the blood and body fluids, while allowing application of the gel composition by spraying, dipping, painting or other selected application methods. Viscosity is a property that affects methods of delivery and application.

Viscosity indicates the flowability of a material. As the viscosity increases, a material exhibits reduced or limited flowability. Specifically, if the gel composition has a viscosity which is too high, it exhibits reduced flowability, which potentially-inhibits delivery or application of the gel. Excessive viscosity adversely affects its ability to wet surfaces and penetrate crevices and areas where parts meet. If the viscosity is very low, the gel flows off the instruments leaving only a thin coating. The viscosity of the gel composition is preferably from about 700 to about 4,000 centipoise (cps), more preferably, from about 1,000 to about 3,500 cps, and most preferably from about 1,500 to 3,000 cps. Compositions having viscosities in excess of 4,000 cps exhibit reduced flowability, which may limit certain application and delivery methods.

The desired viscosity is preferably provided by a thickener, such as a polymer system. The polymer system includes a polymer and any additional components needed to activate the polymer. In one embodiment, the polymer system comprises a polymer and a neutralizing agent. For example, a polymer that is acidic in its free form exhibits little or no gel consistency. The neutralizing agent neutralizes the acidic polymer and produces a polymer system having a gel like nature.

Polymers suitable for use in the polymer system are gel forming, viscosity modifying polymers including, but not limited to, cellulose derivatives, acrylic acid-based polymers, gums, such as guars, guar derivatives, alginates, alginate derivatives, non-ionic surfactants, non-ionic polymers, and mixtures thereof.

Non-limiting examples of suitable cellulose derivatives include carboxy alkyl cellulose polymers, hydroxy alkyl cellulose polymers, and hydrophobically modified derivatives thereof. Some commercially available cellulose derivatives include Natrosol™ Plus CS Grade 330, a hydrophobically modified hydroxyethyl cellulose, Natrosol™250, a hydroxyethyl cellulose, and Klucel™, a hydroxypropyl cellulose, all available from Aqualon.

Examples of suitable acrylic acid-based polymers include but are not limited to those sold by B.F. Goodrich under the tradename Carbopol™, including Carbopol™ETD.™ 2001, 2020, 2050, and 2623. Other exemplary commercially available acrylic acid-based polymers include Carbopol™Aqua 30 and the Carbomer series including Carbopol™934, 940, 941, and 1342 available from B.F. Goodrich.

Suitable non-ionic polymers include vinyl esters, vinyl ethers, vinyl alcohols, acrylamides, methacrylamides, alkyl or aryl acrylates alkyl or aryl methacrylates, alkyl or aryl maleates, acrylonitriles, vinyl pyrrolidone, polyalkenes, such as polymers of styrene, ethylene, or propylene, and multi-functional acids. Exemplary of non-ionic polymers are Laponite™XLS and RDS™, which are synthetic sodium magnesium silicate polymers, available from Southern Clay Products.

Combinations of two or more suitable polymers are optionally employed to form a gel composition.

Alginates, for example, are preferably used in combination with other polymer systems.

The neutralizing agent is any chemical that will sufficiently neutralize the polymer to form a gel. For acidic polymers, neutralizing agents are generally basic, such as triethanolamine (TEA), and alkali metal hydroxides, such as potassium hydroxide (KOH), sodium hydroxide (NaOH), and ammonium hydroxide ($NH_4OH$). For alkaline polymers, an acidic neutralizing agent, such as citric acid, is used.

For example, in the case of hydrophobically modified hydroxyalkyl celluloses, the polymer is first dispersed in an acidic medium such as a citric acid solution at about pH 4. Once dispersed, the composition pH can be adjusted to a more optimal pH for prion destruction (pH 4–8). For example, the pH is adjusted with an alkali, such as KOH, to about pH 5.0 to 5.5.

The components of the polymer system are present in sufficient concentration to provide the gel with the desired viscosity. The optimum amount of polymer present in the formulation depends on whether the gel is non-active or active, and on the type of polymer used. For many polymer systems, the gel composition has a polymer concentration from about 0.05% to about 14%, more preferably, about 0.5% to about 3%, and most preferably about 1.0%. All percentages, unless otherwise noted, refer to percentage by weight.

The concentration of the neutralizing agent depends on the type of polymer and the concentration of the polymer. For example, with a hydrophobically modified hydroxyethylcellulose, about 0.022% of 45% KOH may be used.

In addition to providing viscosity, which helps to retain the formulation on the item being treated, the polymer also assists in solubilizing and/or preventing fixing of the contaminated material, such as proteins, particularly prion proteins.

The composition preferably includes one or more peroxide stabilizers to retard peroxide decomposition in acidic solution. Suitable hydrogen peroxide stabilizers include inorganic or organic substances, described as chelating agents or free radical inhibitors. Suitable stabilizers of this type include alcohols, carboxylic acids, such as hydroxybenzoic acids; phosphonic acids, such as 1-hydroxyethylidene-1,1-diphosphonic acid (HEDP), amino (methyl phosphonic acid), or their soluble salts, such as amino-tri-(methylphosphonic acid), phenylphosphonic acids or salts thereof, such as phenylphosphonic acid; glycol ethers, such as ethyleneglycol monomethylether; and sulphonic acids, such as p-toluene sulphonic acid and dodecylbenzene sulphonic acid; and combinations thereof.

Exemplary stabilizers for acid solutions include 1-hydroxyethylidene-1,1-diphosphonic acid, available from Solutia, Rhodia, or Mayo Chemical, which is effective as a hydrogen peroxide stabilizer, in particular by chelating transition metal ions, such as iron. Other stabilizers include Oxyrite 100, available from B.F. Goodrich, which acts as a rheological stabilizer, and p-hydroxybenzoic acid (alone or in combination with a hydrotropic aryl sulphonic acid and/or hydrophobic alkylaryl sulphonic acid).

The stabilizer is present in sufficient amount to maintain the stability of hydrogen peroxide in the composition to at least 5% by weight until the composition is used and to maintain the stability in the presence of soil at a sufficient concentration to allow the hydrogen peroxide to destroy prions. The amount of the stabilizer present is dependent on the type of stabilizer used and whether the composition is to be formed immediately before use or to be stored for many weeks or months. Additionally, if tap water rather than deionized water is used in the composition, slightly higher concentrations of stabilizer may be appropriate. For example, a stable hydrogen peroxide formulation using deionized water is readily formed using a combination of 0.1–3% by weight Oxyrite 100, more preferably about 0.15% Oxyrite 100, and 0.005 to 0.02% by weight HEDP, more preferably, about 0.008–0.01% by weight HEDP.

In the presence of water, blood, or corrosive fluids, metal substrates tend to begin to corrode instantaneously. The composition, therefore, preferably comprises one or more corrosion inhibitors. Corrosion inhibitors are selected in accordance with the nature of the materials in the metal substrate. It is therefore preferable to have one or more corrosion inhibitors in the composition, such that the composition may be applied on a variety of metal substrates. Corrosion inhibitors are present at sufficient concentrations to inhibit corrosion of the medical instruments or other devices during the period of exposure to the composition.

Exemplary copper and brass corrosion inhibitors are generally nitrogen or oxygen containing organic compounds, such as amines, nitro compounds, benzoates, azoles, imidazoles, diazoles, triazoles, carboxylic acids, and the like. Azoles such as mercaptobenzothiazole, and aromatic triazoles and their salts, such as benzotriazole, tolyltriazole, and sodium tolyltriazole, are particularly suitable as copper and brass corrosion inhibitors. A combination of azole-based corrosion inhibitors is available, for example, as Cobratec™ 939 from PMC.

The concentration of the copper and brass corrosion inhibitor is preferably from about 0.002% to about 1.0%, and most preferably from about 0.1% to about 0.5%.

Suitable corrosion inhibitors for steel substrates include phosphates, phosphonic acids, sulfates and borates. Suitable phosphates include alkali metal phosphates, such as those of sodium and potassium. Other examples of suitable phosphates include monosodium phosphate, disodium phosphate, sodium hexametaphosphate, and potassium equivalents thereof. Sodium hexametaphosphate also serves as a chelating agent for water hardness salts, and the like. Hydroxyethylidine di-phosphonic acid, sold under the tradename Dequest™ 2016 by Solutia Inc., is an exemplary steel corrosion inhibitor. Corrosion inhibitors for steel, where used in the composition, are preferably present at concentrations of from about 0.005% to about 1.0%, more preferably from about 0.0065% to about 0.1%, and most preferably from about 0.007% to about 0.01%.

Exemplary aluminum corrosion inhibitors include 8-hydroxyquinoline and orthophenylphenol.

The composition preferably includes a humectant. This helps the gel composition to retain moisture when the gel is applied to an instrument. Suitable humectants include polyhydroxy compounds, such as sorbitol, glycerine, glucitol, polyethylene glycol, propylene glycol, dipropylene glycol, 1,3-butylene glycol, hexylene glycol, and mixtures thereof. Sorbitol is obtainable from Roquette Corp., ADM (Ashland).

The humectant is preferably present at from about 5% to about 30% by weight of the composition, more preferably, about 10%.

While not fully understood, it is considered that the sorbitol, or other humectant, helps to solubilize contaminated material, such as proteins, particularly prion proteins, and/or prevent the fixing of contaminated material on the surface of the item being treated.

The composition optionally includes an active antimicrobial agent, in addition to hydrogen peroxide, which exhibits an antimicrobial function, such as sanitizing, disinfecting, or sterilizing. Sanitizing connotes preventing fungal growth and actively working against some types of bacteria. Disinfecting connotes killing or removing pathogenic microorganisms. Sterilizing connotes killing all microorganisms, including bacterial endospores, which are the living organisms most resistant to known sterilants.

The antimicrobial agent in the composition need not provide complete sterilization or disinfection during the time of contact. Rather, the antimicrobial agent helps to reduce human exposure to microorganisms during the cleaning stage. Suitable antimicrobial agents include, but are not limited, to hydroxyacetic acid, perhydroxyacetic acid, peroxyacetic acids, chlorine dioxide, ozone, and combinations thereof. Suitable peroxy acetic acids include peracetic and performic acid. A preferred combination of active ingredients is hydrogen peroxide and peracetic acid. Other actives which may be used include quaternary ammonium compounds (which aid with cleaning), phenols, Triclosan™, and chlorohexidine gluconate.

The antimicrobial agent is present in quantities sufficient to achieve a desired level of antimicrobial treatment of the instruments. For example, higher concentrations are used to provide sterilization, while lower concentrations are appropriate for disinfecting or sanitization.

The composition optionally includes a surface energy reducing agent or wetting agent ("surfactant") to increase penetration into crevices of items being treated. This is particularly important when cleaning and decontaminating complex medical instruments which may contain microbial contaminants in crevices, joints, and lumens. Surfactants in the gel composition, when coated on the soiled instruments, penetrate the surface of dirt and debris and help break up and remove the soils.

Exemplary surfactants include anionic, cationic, non-ionic, amphoteric, and/or zwitterionic surfactants. Examples of non-ionic surfactants include fatty alcohol polyglycol ethers, nonylphenoxypoly (ethyleneoxy) ethanol, a non-ionic surfactant, and ethoxylated polyoxypropylene, a non-ionic surfactant. Specific examples include Genapol UD-50™, Igepal™ (nonylphenoxypoly (ethyleneoxy) ethanol), Fluowet™, Antarox™ (ethoxylated polyoxypropylene), and Pegol™. The surfactants set forth above or others may be used alone or in combination with each other.

In cases where the instruments are to be subsequently washed in an automated washer, surfactants used in the composition are preferably low-foaming surfactants, such as non-ionic and amphoteric surfactants, such as a mixed $C_8$ amphocarboxylate.

Surfactants are preferably present in the gel compositions at concentrations from about 0% to about 1.0%, more preferably from about 0.05% to about 0.5%, and most preferably from about 0.08% to about 0.2%.

The composition may also include other ingredients known in the art, such as water soluble dyes, for example, to make the composition more readily visible on the instruments, perfumes, and fragrances, for example, to mask unpleasant odors associated with soiled or contaminated instruments, and the like.

The balance of the composition comprises water, preferably in the range from about 50% to about 93%. Preferably, deionized water or other purified water is used in the gel composition, but tap water may also be utilized.

For prion destruction, the composition preferably has a pH of about 4–8, more preferably, from about 5.0–6.0. The pH can be adjusted, for example, by addition of acid or alkali, to reach the desired pH.

An exemplary composition includes:

| Component | % By Weight |
|---|---|
| Hydrogen peroxide | 5–8% |
| Hydrophobically modified hydroxyethyl cellulose (e.g., Natrosol Plus CS) | 0.5–3% |
| Citric acid (for dispersion Of Natrosol) | 0.00025 to 0.0035% |
| Potassium hydroxide | to adjust pH to about 5.0–5.5 (about 0–0.3%) |
| Humectant (e.g., Sorbitol) | 5–30% |
| Chelating/stabilizing agent (e.g., HEDP) | 0.008–0.01 |
| Rheological stabilizer (e.g., Oxyrite 100) | 0.1–0.3 |
| Azole corrosion inhibitor (e.g., Cobratec 939) | 0.1–1% |
| Deionized water | Q.S. (about 78–85%) |

A particularly preferred formulation includes:

| Component | % By Weight |
|---|---|
| Hydrogen peroxide | 7% |
| Hydrophobically modified hydroxyethyl cellulose (Natrosol Plus CS) | 1% |
| Citric acid | 0.0003% |
| Potassium hydroxide | to adjust pH to about 5.0–5.5 (about 0–0.3%) |
| Sorbitol | 10% |
| HEDP | 0.008% |
| Rheological stabilizer (Oxyrite 100) | 0.15% |
| Azole corrosion inhibitor (Cobratec 939) | 0.2% |
| Deionized water (e.g., MilliQ) | Q.S. (about 78–85%) |

The composition is formed by mixing the desired components in the amounts previously specified herein. Upon formation, the composition may be used immediately or stored for later use.

The composition is especially suited for a post-operative treatment step for medical, dental, mortuary, or pharmaceutical instruments and/or devices, prior to cleaning and decontamination. The gel composition provides a means for keeping the blood and other protein-rich body fluids, which are present on soiled medical instruments after a surgical procedure, moist for extended periods of time as well as destroying prions on the surface.

The gel composition keeps blood or other body fluids moist for several hours, typically about three to four hours, and up to eight hours in some cases, which in most instances is sufficient to transport the instrument to a washing system. Water in the gel composition interacts with the fluids on the instrument to solubilize and keep the blood and other biological fluids moist. The length of time in which fluids are kept moist by the gel is dependent on the thickness of the applied gel film. Thicker gel films result in longer periods of time before drying. In typical applications, the exposed surface of a gel film begins to skin over or dry first, often in about two to about four hours, while the remaining gel remains wet. Preferably, the gel compositions last over eight hours before completely drying out.

In an alternative embodiment, the composition is in the form of a liquid composition. In this embodiment, the devices are preferably fully immersed in the composition or subjected to spraying with the composition for the desired period of exposure.

The composition is applied to the instruments by any suitable dispenser for dispensing liquid, gel, or foam compositions. Exemplary dispensers include trigger spray bottles, pump spray containers, pressurized spray cans, squeeze bottles, and spray devices utilizing a compressed air pump. An exemplary method of applying the gel composition to the instrument includes spraying. Other methods of application include dipping the instruments in the gel composition or painting the gel composition with a brush or other application. The method includes treating surgical instruments such that prions present are deactivated and blood or body fluids remaining on post-surgical instruments do not dry out.

For example, prion contaminated post-surgical medical instruments are treated by applying the composition in the form of a gel to the instruments, allowing the gel to remain on the instruments for a sufficient time to destroy substantially all prions on the surfaces of the instruments, transporting the treated instruments coated with the applied gel composition to a cleaning station, and cleaning and preferably sterilizing the treated medical instruments.

A sufficient amount of gel composition is preferably applied such that all contaminated regions of the instruments are sufficiently coated with the gel composition to contain the fluid and keep it moist during prion decontamination and until cleaning takes place.

Optionally, other post-operative cleaning processes are used prior to or after the use of the composition. For example, a liquid cleaner may be used to treat internal passages of instruments, or the instruments may be soaked in a liquid cleaner, such as an enzymatic cleaner.

Optionally, additional gel may be applied to a contaminated region if desired. For example, where a washer or sterilizer is not available for cleaning or sterilizing the instruments, applying additional gel, such that a fluid does not dry out, increases the time which may elapse prior to subsequent cleaning.

Preferably, the composition resides on the treated instrument in a gel like state until the cleaning and/or microbial decontamination process. During cleaning the gel and any soils, blood, or other fluids are removed from the instrument surface. The gel composition, specifically, the surfactants contained therein, facilitates cleaning and removal of debris during the cleaning process.

Cleaning and sterilization is accomplished by any known method in the art. Cleaning, for example, may be accomplished in an automated washer using suitable detergents. Sterilization may be accomplished after the wash cycle by exposing the instrument to a sterilizing agent, such as, for example, liquid or vapor peracetic acid, vapor hydrogen peroxide, or the like. Sterilization may also be suitably accomplished by steam sterilization methods.

In addition to destroying prions effectively, the hydrogen-peroxide containing formulations described herein have been found to be effective at killing or otherwise rendering harmless a variety of other microbiological species, including bacteria, fungi, and viruses, and mycotoxins formed as these microorganisms die.

Typical bacteria and bacterial spores which can be disinfected with the present composition include *Bacillus*, such as *Bacillus anthracis*, *Bacillus subtilis*, *Pseudomonas*, e.g., *Pseudomonas aeruginosa*, *Pseudomonas fluorescens*, *Salmonella*, e.g., *Salmonella pullorum*, *Salmonella typhosa*, *Enterobacter*, e.g., *Enterobacter cloacae*, *Enterococcus*, e.g., *Enterococcus faecalis*, *Moraxella*, e.g. *Moraxella catarrhalis*, *Haemophilus*, e.g., *Haemophilus influenza*; *Klebsiella*, e.g., *Klebsiella edwardsii*, *Klebsiella pneumoniae*, *Streptococcus*, e.g., *Streptococcus pneumoniae*, *Streptococcus durans*, *Streptococcus faecium*, and *Streptococcus pyogenes*; *Staphylococcus*, e.g., *Staphylococcus aureus*, *Staphylococcus pyogenes*, *Escherichia*, e.g., *Escherichia coli*, *Proteus*, e.g., *Proteus mirabilis*, and *Listeria*, e.g., *Listeria monocytogenes*, and the like.

Fungi and fungal spores which may be disinfected by the present composition include *Aspergillus*, e.g., *Aspergillus fumigatus*, *Aspergillus glacus*, *Aspergillus niger*, *Fusarium*, e.g., *Fusarium solani*, *Penicillium*, e.g., *Penicillium variable*, *Stachybotrys*, and the like.

Bacterial and fungal spores which may be disinfected.

Viruses which are disinfected by this composition include AIDS, Avian Infectious Bronchitis, Canine Coronavirus, Herpetoviridae (Infectious Bovine Virus), Rhinotracheitis, Distemper, Feline Herpes, Iridoviridae (African Swine Fever), Parvoviridae, (Canine Parvovirus), Poxviridae Pseudo (Cowpox), Coronaviridae (Transmissible Gastro-Enteritis), Orthomyxoviridae (Avian Influenza), Paramyxoviridae, Picornaviridae (Swine Vesicular Disease), Foot & Mouth Disease, Retroviridae, and the like.

Without intending to limit the scope of the invention, the following examples indicate the effectiveness of the composition against prion-like species.

EXAMPLE 1

Effect of Hydrogen Peroxide on IFDO

The following formulations are prepared, as shown in TABLE 1. Formulation 1 includes 7% hydrogen peroxide. Formulation 2 is prepared without hydrogen peroxide, to act as a control.

TABLE 1

| Component | Formulation 1 | Formulation 2 |
|---|---|---|
| Deionized water | 68.6197 | 88.6139 |
| Citric Acid | 0.0003 | 0.0061 |
| Natrosol 330 | 1.0 | 1.0 |
| KOH | 0.022 | 0.022 |
| Sorbitol | 10.0 | 10.0 |
| HEDP | 0.008 | 0.008 |
| Oxyrite | 0.15 | 0.15 |
| Cobratec 939 | 0.2 | 0.2 |
| Hydrogen peroxide (35% solution) | 20.0 | 0 |
| KOH | As needed to bring the pH to 5.5 | — |

The two formulations are tested against an ileal fluid dependent organism (IFDO). This organism has been shown to be an effective model for human and other prions since it shows comparable behavior patterns to prions when exposed to a variety of environments, such as disinfection and sterilization. The organism was first extracted from ileal fluid (hence its name) by Burdon (Burdon, *J. Med. Micro.*, 29: 145–157 (1989)). The organism is readily cultured and detected in the laboratory. For example, the organism is cultured in a modified *Mycoplasma* base broth and quantified by serial dilution and plating onto a simple agar.

In the present Example, the efficacy of the two formulations is studied by suspension testing at room temperature, in which a suspension of the IFDO is suspended in the cleaning solution and samples are taken at time intervals for evaluation. The samples are quantified by serial dilution and plating onto modified *Mycoplasma* agar. The plated samples are incubated at 37° C. for 48 hours and detectable colonies (visible as black spots) are counted. FIG. 1 shows a plot of the number of IFDO organisms remaining (expressed as $Log_{10}$ of the number remaining), at intervals between 0 and 5 hours for each of the two formulations.

As can be seen from FIG. 1, the 7% composition (Formulation 1) rapidly destroys the IFDO, with no detectable colonies observable after 2 hours of exposure. Formulation 2 has no detectable influence on the IFDO.

It is to be appreciated that the tests are carried out in a suspension and thus the benefits of the other ingredients in the composition (thickeners, humectants, etc.) on the cleaning capacity of the composition for instruments contaminated with body fluids and tissue is not apparent in this test.

EXAMPLE 2

Effect of Hydrogen Peroxide Concentration on IFDO

Formulations are prepared as for Formulation 1 of Example 1, but with different concentrations of hydrogen peroxide (the quantity of water is adjusted accordingly).

Suspensions of IFDO in the different formulations are tested as for Example 1. FIG. 2 shows the effect of hydrogen peroxide concentration over time. The formulations containing 1%, 2%, 3%, and 4% by weight hydrogen peroxide, respectively, all show measurable levels of IFDO after 3 hours of exposure. At 5% hydrogen peroxide or above, the formulations show no detectable IFDO after 3 hours of exposure. Only the 7% hydrogen peroxide formulation shows no detectable IFDO after 2 hours of testing.

EXAMPLE 3

Effect of Hydrogen Peroxide on Prion Contaminated Materials

Stainless steel wires are inoculated with brain material contaminated with Scrapie (sheep) prion protein. The wires are air dried overnight. Sets of the wires are soaked for one hour in one of the following: deionized water; Formulation 1 of Example 1 (includes 7% hydrogen peroxide plus surfactants, etc.); and 7% hydrogen peroxide in deionized water. The wires are removed from the liquid, rinsed in deionized water and extracted to remove remaining protein and biological material. Samples of the extracts are separated by SDEPAGE and Western blotted with an anti-scrapie protein antibody to detect the presence of absence of scrapie following the treatment. A control sample, which undergoes no soaking, is also extracted and tested. The results are as shown in TABLE 2

TABLE 2

| Treatment | Percentage of Samples Tested where Prion (Scrapie) is Detected |
|---|---|
| Control (no treatment) | 100% |
| Water | 95% |
| 7% Hydrogen Peroxide | 100% |
| Formulation 1 | 0% |

The results shown in TABLE 1 indicate that the 7% hydrogen peroxide alone had no effect on the percentage of samples showing presence of prion in the period of the test.

The additional components of Formulation 1 clearly help to reduce prion concentration, for example, by solubilizing and/or preventing fixing of the contaminated biological material on the surface of the treated wires.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A composition for treatment of prion contaminated surfaces, comprising:

5–30% by weight hydrogen peroxide;

a thickener in a sufficient amount to provide a viscosity of 700–4000 cps;

5–30% by weight of a humectant, the humectant including sorbitol;

at least 0.1% by weight of a corrosion inhibitor; and a hydrogen peroxide stabilizer.

2. The composition of claim 1, wherein the pH of the composition is from 5–6.

3. The composition of claim 1, wherein the hydrogen peroxide is at a concentration of 6–8% by weight.

4. The composition of claim 1, wherein the corrosion inhibitor is selected from the group consisting of azoles, diazoles, and triazoles.

5. The composition of claim 1, wherein the hydrogen peroxide concentration is about 7% by weight of the composition.

6. The composition of claim 1, wherein the composition comprises a thickener selected from the group consisting of cellulose derivatives, acrylic acid-based polymers, guars, guar derivatives, alginates, alginate derivatives, non-ionic surfactants, non-ionic polymers, and combination thereof.

7. The composition of claim 6, wherein the thickener includes a hydroxyethylcellulose or hydrophobically modified derivative thereof.

8. The composition of claim 1, wherein the humectant further comprises an additional humectant selected from the group consisting of, glycerine, glucitol, polyethylene glycol, propylene glycol, dipropylene glycol, 1,3-butylene glycol, hexylene glycol, and mixtures thereof.

9. The composition of claim 1, wherein the composition comprises:

hydrogen peroxide at a concentration of 6–8% by weight;

5–30% sorbitol;

0.1–1% of an azole corrosion inhibitor; and further comprising a chelating agent.

10. An aqueous gel composition for treatment of a prion-contaminated surface of a medical device which has been used in a surgical procedure, comprising:

5–30% by weight hydrogen peroxide;

a thickener in a sufficient amount to provide a viscosity of 700–4000 cps;

5–30% by weight of a humectant for retaining moisture on the surface, the humectant including sorbitol;

at least 0.1% by weight of a corrosion inhibitor; and a hydrogen peroxide stabilizer;

the composition formulated so as to form a coating on the medical device without the medical device drying out for a period of at least one hour.

* * * * *